United States Patent [19]

Allen

[11] Patent Number: 4,991,686
[45] Date of Patent: Feb. 12, 1991

[54] DISPOSABLE STETHOSCOPE

[76] Inventor: Derek R. Allen, 30994 Steeplechase Dr., San Juan Capistrano, Calif. 92675

[21] Appl. No.: 282,741

[22] Filed: Dec. 12, 1988

[51] Int. Cl.$^5$ ................................................ A61B 7/02
[52] U.S. Cl. ..................................... 181/131; 181/130
[58] Field of Search ........................ 181/130, 131, 137

[56] References Cited

U.S. PATENT DOCUMENTS 3,993,161 11/1976 Shore .............................. 181/131 X
4,029,169 6/1977 Huntress .............................. 181/135
4,569,413 2/1986 Allen ................................... 181/131

Primary Examiner—Benjamin R. Fuller
Attorney, Agent, or Firm—George F. Bethel; Patience K. Bethel

[57] ABSTRACT

A stethoscope including a stethoscope head, a pair of ear tips, and binaural tube means providing two individually separate air passages including a longer passage and a shorter passage extending between the stethoscope head and each ear tip. A substantially U-shaped binaural yoke includes channel members for receipt of the binaural tube members whereby the longer tube can be retained within the yoke without producing any sharp bends which would cause a loss of sound transmission. the stethoscope is designed to be made entirely of plastic materials.

14 Claims, 3 Drawing Sheets

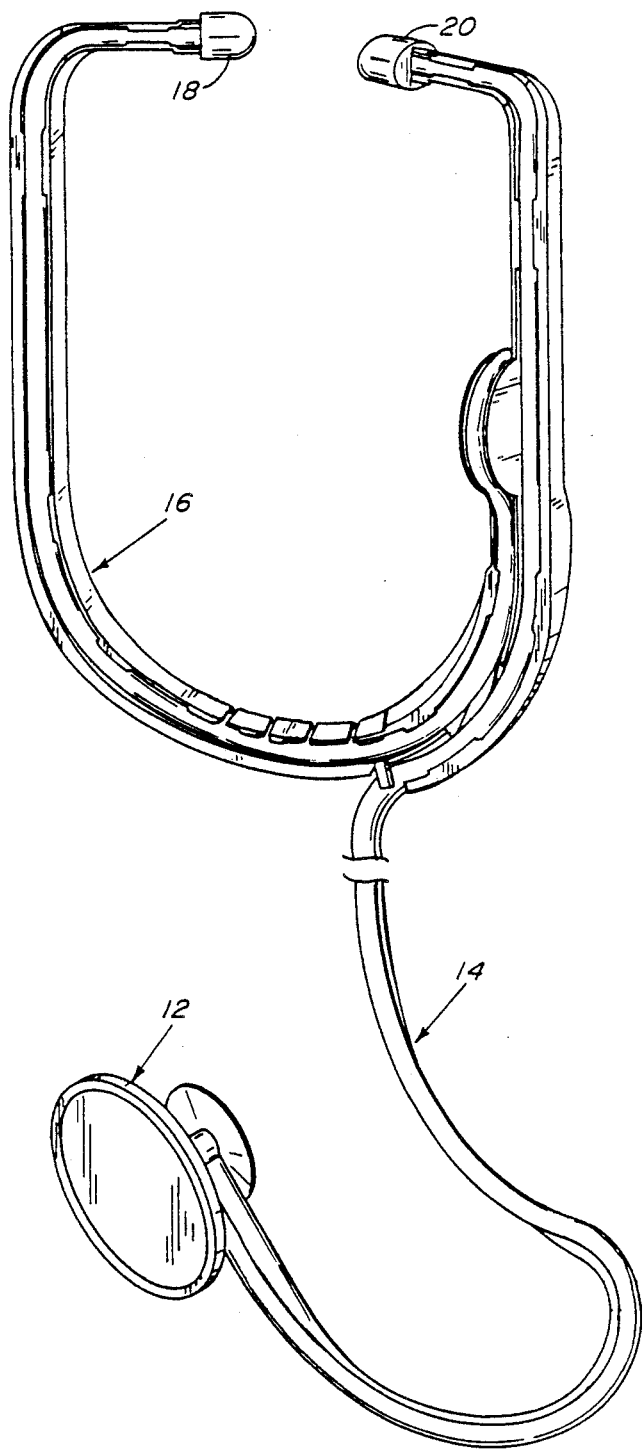
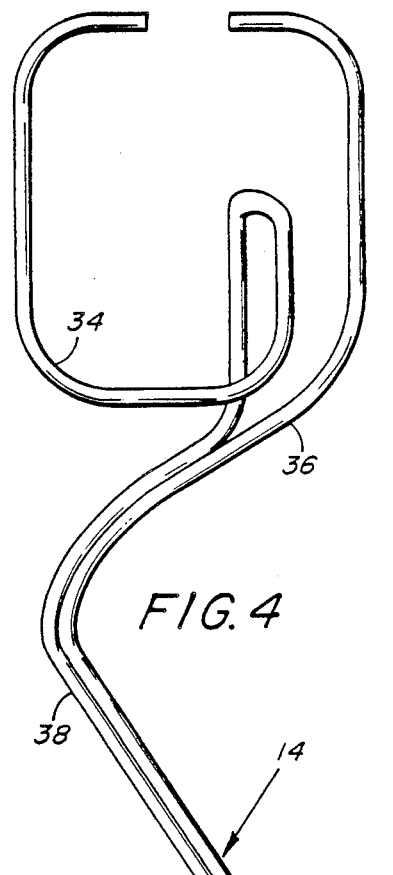
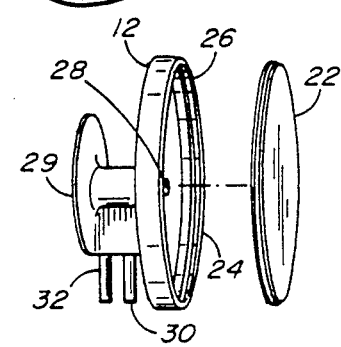
FIG. 3
FIG. 4
FIG. 5

DISPOSABLE STETHOSCOPE

FIELD OF THE INVENTION

This invention relates to the field of stethoscopes, and especially to medical stethoscopes designed for auscultation. Specifically, the invention relates to a disposable stethoscope which can be used in the audio output frequency transmission range of about fifty cycles per second to about three thousand cycles per second (Hertz).

DESCRIPTION OF THE PRIOR ART

In my prior U.S. Pat. No. 4,569,413 I have disclosed and claimed a stethoscope which includes a stethoscope head and a pair of ear tips which are connected by binaural tube means which provide individually separate air passages from the stethoscope head to the ear tips. The length of each of the air passages is selected so that the resonant peaks of sound transmitted from the stethoscope head to one ear lie in the resonant valleys of sound transmitted from the stethoscope head to the other ear. This is achieved by utilizing separate air passages which have a length ratio in the range of about 0.63 to about 0.73. The stethoscope can be utilized in conjunction with a dual stethoscope head having a bell receiver for transmitting low frequency sounds and a diaphragm receiver for transmitting high frequency sounds. Alternatively, the stethoscope can be utilized with a single stethoscope head having a diaphram or a bell receiver. The choice will depend upon the type of sounds to be detected with use of the stethoscope.

My prior stethoscope described in U.S. Pat. No. 4,569,413 is further characterized by the inclusion of a binaural yoke having a juncture where the binaural tube extending from the stethoscope head bifurcates into two diverging channels, each channel extending to one ear tip. The binaural yoke includes a cylinder having a slit therein. A yoke spring is disposed longitudinally within the yoke, a portion of which spring passes through and is held by the slit in the cylinder. A ring attached to the interior wall of the yoke and substantially centrally disposed at the juncture of the yoke with the binaural tube means tightly surrounds the cylinder and yoke spring to sound seal one portion of the yoke from the other at the juncture. This arrangement provides a continuation of each individually separate air passage extending from the stethoscope head to each respective ear tip.

SUMMARY OF THE INVENTION

My new stethoscope shares similarities with the above stethoscope. It includes a stethoscope head and a pair of ear tips which are connected by tube means which provide individually separate air passages. Each of the air passages is of a different length to provide a length ratio in the range of about 0.63 to about 0.73. My stethoscope differs from my prior art stethoscope in that the tube means provide individually separate sealed air passages for the entire length of each tube, being formed of a continuous length of tubing for each passage. The tubes are separably joined along one contiguous lengthwise surface of each tube for a portion of its length extending from the stethoscope head.

My new stethoscope includes a binaural yoke which is in the form of a U-shaped member provided with a first open channel extending from a first ear tip to a point spaced from a second ear tip. Here, the sides of the first channel extend into two spaced apart round discs with a recessed cylindrical member disposed therebetween to form a spool-like channel adapted to receive the longer length of tubing. An aperture in the base of the first channel adjacent the spool-like member permits insertion through the base of the first open channel and wrapping of the longer length of tubing around the spool-like member where it seats against the cylindrical member. From the cylindrical member the longer tubing is seated within the first channel and extends to the first ear tip.

A second open channel extends from the second ear tip toward the first ear tip and terminates in an open end adapted for receiving the portion of the binaural tube which is joined. The second open channel is parallel to the first channel along at least a portion of its length. A portion of the first and second channels which run parallel and have a common wall is broken away to allow communication between the first and second channels. This common opening is adapted to receive the binaural tubes at their point of separation. The longer tube is held as above described. The shorter tube seats within the second channel and extends to the second ear tip.

The first and second channels are provided with retainment means in the form of a plurality of projecting tabs adapted for holding and retaining the tubing.

The ends of the U-shaped yoke are provided with rounded ear tips which have a recess adapted to slip-fit over the ends of the U-shaped yoke containing the ends of the binaural tubes. Each ear tip is further provided with a central tube adapted to fit within and seal the respective ends of the tubular air passages which slip-fit thereover. There is thus provided a continuous uninterrupted sealed length of tubing from the stethoscope head to each ear tip.

The tubing is preferably made of an extruded length of plastic or rubber-like material. Preferably the two lengths of tubing are co-extruded so that they are barely joined along their contiguous side in a manner whereby they can be separated or split apart without disturbing the integrity of the sound passages.

The base of the U-shaped yoke is provided with several slots adapted to provide a spring capability to the yoke. This enables the spreading apart of the legs of the U-shaped member for placement of the ear tips by a user and at the same time provide a spring force sufficiently strong to keep the yoke in place.

A major advantage to my new stethoscope is the capability of being made entirely of plastic which permits greatly reduced cost of manufacture. This characteristic not only makes the stethoscope attractive in itself but also as a disposable stethoscope. Disposable instruments, apparatus and the like are currently very much in demand to avoid the spread of disease in hospitals and other healthcare facilities.

BRIEF DESCRIPTION OF THE DRAWINGS

The invention will be better understood when taken with the accompanying drawings.

FIG. 3 shows a perspective view of the stethoscope of the invention.

FIG. 4 shows the binaural tubing of the stethoscope, formed of two tubes of different length.

FIG. 5 shows a perspective view of the stethoscope head with the two separate projecting tubular members for insertion within the binaural tubing.

DETAILED DESCRIPTION OF THE DRAWINGS

Figure 1:
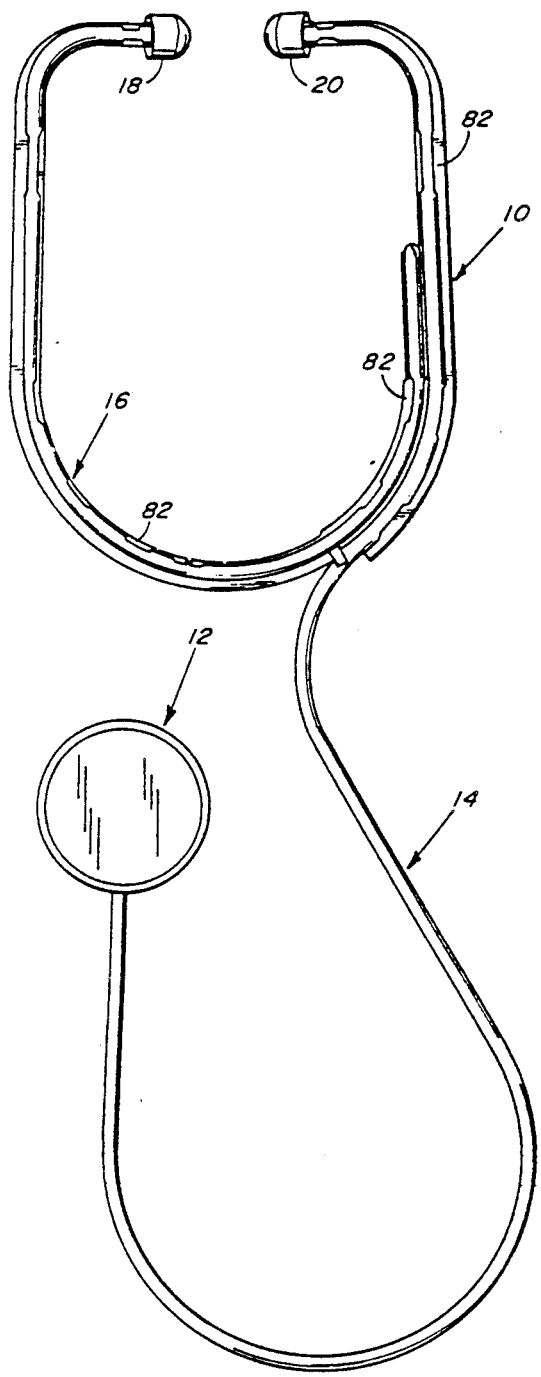
FIG. 1 shows a plan view of the stethoscope of the invention.
Figure 2:
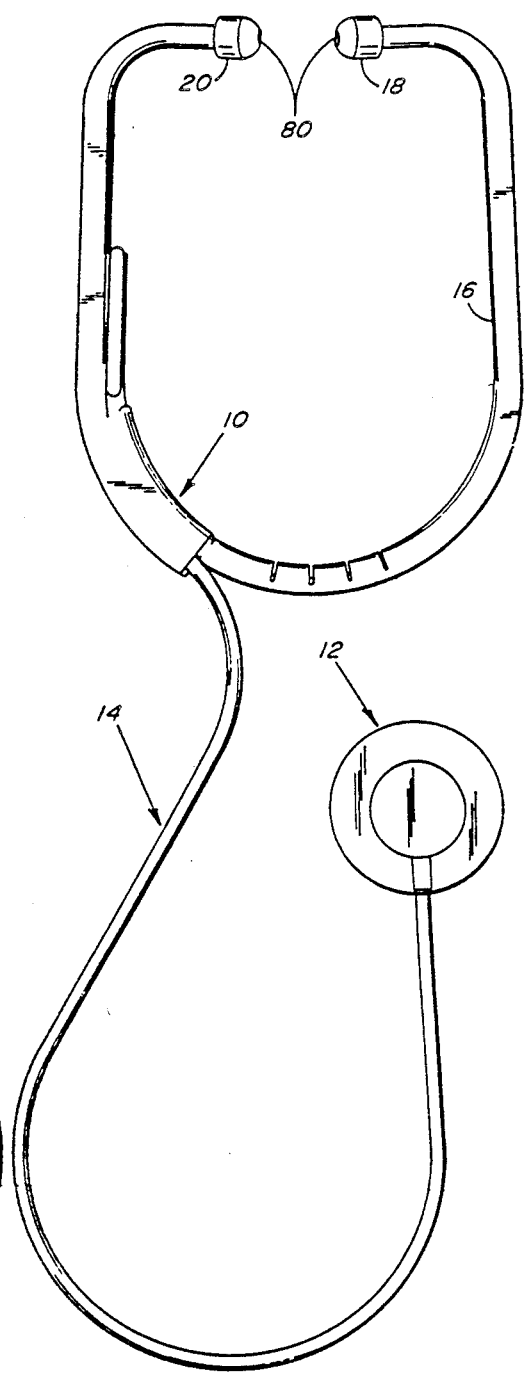
FIG. 2 shows a reverse plan view of the stethoscope of the invention.

Referring now to FIG. 1, there is shown a stethoscope indicated generally at 10. The stethoscope 10 includes a stethoscope head 12 from which extends binaural tubing 14. Binaural tubing 14 is held by binaural yoke 16 which includes ear tips 18 and 20 which are sealed to the ends of the binaural yoke 16.

Figure 8:
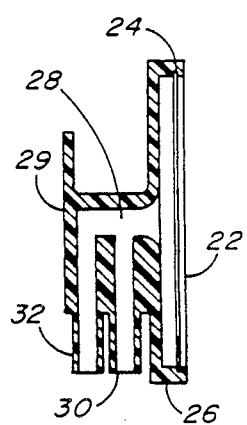
FIG. 8 shows a cross section of the stethoscope head of FIG. 5.

The stethoscope head 12 as shown in detail in FIGS. 5 and 8 includes a diaphram 22 which is held within a groove 24 of diaphram receiver 26. In the center of the diaphram receiver 26 is an opening or conduit 28. Conduit 28 communicates with lateral openings or conduits 30 and 32. Conduits 30 and 32 are adapted for insertion into the open ends of binaural tubes 14. A disc member 29 is disposed opposite the diaphram 22 and aids in grasping the stethoscope head 12.

As detailed especially in FIG. 4, binaural tubing 14 includes two tubes of different length. The longer tube 34 and the shorter tube 36 are joined along a portion of their length as indicated at 38. The joined portion 38 extends from the stethoscope head 12 to the binaural yoke 16.

Figure 6:
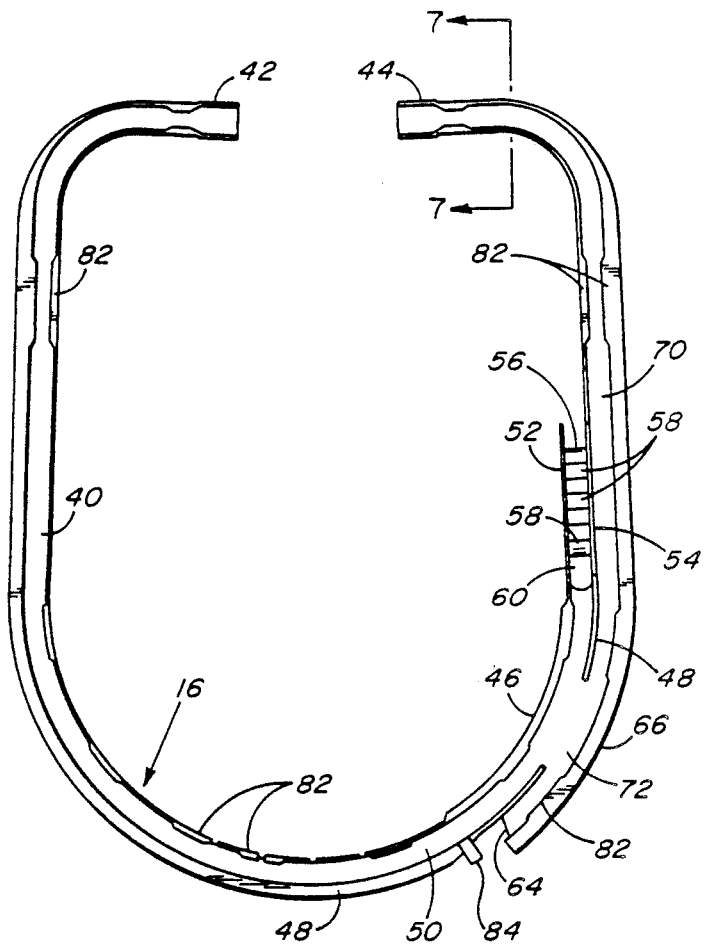
FIG. 6 shows a plan view of the yoke of the stethoscope with the binaural tubing, ear tips and stethoscope head removed therefrom.

The binaural yoke 16 can be seen particualarly in FIGS. 1, 2, 3, and 6. As shown in FIG. 6, the binaural yoke 16 has a generally U-shape and includes a first open U-shaped channel 40 which extends from one end 42 of the yoke 16 toward the opposite end 44 of the yoke 16. The first open channel 40 includes sidewalls 46 and 48 and a bottom wall 50. Prior to reaching the end 44 of yoke 16, the side walls 46 and 48 extend into round discs 52 and 54. Between round discs 52 and 54 is a slightly recessed relatively thin cylindrical member 56.

Cylindrical member 56 can be provided with through channels or openings 58 if desired. The cylindrical member 56 with the round discs 52 and 54 are adapted to receive the longer length of binaural tube 34.

In the bottom 50 of first open channel 40 is an opening or aperture 60 adapted for insertion of longer binaural tube 34 prior to encircling cylindrical member 56.

Binaural yoke 16 also includes a second open substantially U-shaped channel 62 which extends from end 44 toward end 42 and terminates in a opening 64 adapted for entry of binaural tubing 14. Second channel 62 includes sidewalls 48 and 66 and bottom wall 70. It can be seen that sidewall 48 is common to both the first channel 40 and the second channel 62. There is a break in common sidewall 48 indicated at 72. It is here where the longer binaural tube 34 is separated from shorter binaural tube 36.

Binaural tube 34 is then inserted through opening 60 in the bottom wall 50 of first open channel 40. The tube 34 is then wrapped around cylindrical member 56 where the tube is held between discs 52 and 54. The tube 34 is then inserted within first open channel 40. Here tube 34 is made to overlie itself for a short length where it doubles back on itself. Thereafter it extends within first open channel 40 to end 42 of binaural yoke 16. At end 42 of yoke 16 the tube 34 and end 42 are inserted into ear tip 18.

Shorter tube 36 is inserted within second open channel 70 where it extends to end 44 of binaural yoke 16. At end 44 of yoke 16 the tube 34 and end 44 are inserted into ear tip 20.

Thus, tube 34 forms a separate sealed air passage from stethoscope head 12 to ear tip 18. In the same manner, tube 36 forms a separate sealed air passage from stethoscope head 12 to ear tip 20.

Figure 7:
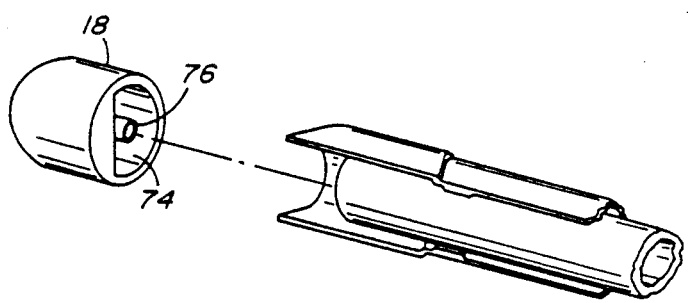
FIG. 7 shows a partially broken away perspective view of one of the ear tips and its connection to one end of the yoke and one binaural tube.

The manner of fastening the ear tips 18 and 20 to the respective ends 42 and 44 of yoke 16 and tubes 34 and 36 can be seen in FIG. 7. As shown, one end of ear tip 18 is provided with a substantially U-shaped opening 74 which is adapted to receive the U-shaped end 42 of binaural yoke 16. Centrally disposed within opening 74 is a tubular projection 76 forming a central passage extending completely through the ear tip 18. The projection 76 is adapted for insertion snugly within the end of tube 36 which slip fits over projection 76.

The other end of ear tip 18 is substantially rounded and has an opening 80 which forms the end of projection 76. This rounded end of ear tip 18 is adapted to fit into the ear of a user. The ear tip 20 is attached in the same manner as for ear tip 18.

Binaural yoke 16 is further provided with a plurality of tabs 82 which project over open channels 40 and 70 and which are adapted to hold binaural tubes 34 and 36 within channels 40 and 70. There is also a projecting tab 84 which performs basically the same function.

A plurality of slots 86 are located within the midregion of binaural yoke 16 in order to control the spring tension provided by the yoke 16. The presence of the slots 86 permit opening of the yoke 16 for purposes of inserting the ear tips 18 and 20 into the ears of a user and then retaining them there by means of the spring tension.

While the invention is shown with a diaphram receiver, it should be understood that the invention is not limited thereto. A bell receiver can be used as well as a dual stethoscope head including both a bell receiver and a diaphram receiver.

The stethoscope as shown is designed to be made entirely of plastic materials. This is for the purpose of providing low cost and light weight. The binaural tubes are preferably made of an extrudable plastic such as PVC (polyvinyl chloride) but other plastics can be used as well which are known to those skilled in the art.

The yoke is preferably performed from a rigid plastic such as polypropylene. Other rigid plastics can be substituted which will provide the memory needed for the spring action of the yoke and can withstand the repeated bending associated with the opening of the yoke. Such plastics are known to those skilled in the art.

The diaphram of the stethoscope can be fabricated from ABS plastic (a polymer of acronitrile, butadiene, and styrene). Other plastics can be substituted therefor which are known to those skilled in the art.

Various modifications of the invention will be apparent to those skilled in the art and can be resorted to without departing from the spirit and scope of the invention as defined in the following claims.

I claim:

1. A stethoscope comprising:
   a stethoscope head
   a pair of ear tips;

binaural tube means providing two individually separate air passages extending between said stethoscope head and each ear tip and including a longer passage and a shorter passage;
a substantially U-shaped binaural yoke having channel means adapted for holding said binaural tube means;
said substantially U-shaped yoke having a first end and a second opposite end;
said channel means comprising:
a first open channel extending from said first end of said substantially U-shaped yoke toward said second opposite end of said yoke and adapted for receiving and holding said longer binaural tube means;
means within said first open channel for accommodating a doubled over portion of said longer binaural tube means without producing any sharp bends which would cause a loss of sound transmission;
a second open channel extending from said second end of said yoke toward said first end and adapted for receiving and holding said shorter binaural tube means;
said second open channel terminates in an open end for receiving both said longer binaural tube means and said shorter binaural tube means; and,
a lengthwise section of said first and second channels have a common wall, said common wall having an opening therein for communication between said first and second open channels which is adapted for receiving said longer binaural tube means from said second open channel for receipt within said first open channel.

2. A stethoscope as claimed in claim 1 wherein:
said longer and said shorter binaural tube means are at least partly joined between said stethoscope head and said yoke.

3. A stethoscope comprising:
a stethoscope head;
a pair of ear tips;
binaural tube means providing two individually separate air passages extending between said stethoscope head and each ear tip and including a longer passage and a shorter passage;
a substantially U-shaped binaural yoke having channel means adapted for holding said binaural tube means, said substantially U-shaped yoke having a first end and a second opposite end and wherein said channel means comprise a first open channel extending from said first end of said substantially U-shaped yoke towards said second opposite end of said yoke and adapted for receiving and holding said longer binaural tube means;
means within said first open channel for accommodating a doubled over portion of said longer binaural tube means without producing any sharp bends which would cause a loss of sound transmission;
a second open channel extending from said second end of said yoke towards said first end and adapted for receiving and holding said shorter binaural tube means;
said second open channel terminating in an open end for receiving both said longer binaural tube means and said shorter binaural tube means;
a lengthwise section of said first and second channels having a common wall, said common wall having an opening therein for communication between said first and second open channels which is adapted for receiving said longer binaural tube means from said second channel for receipt within said first open channel;
said longer and said shorter binaural tube means being at least partly joined between said stethoscope head and said yoke;
said means within said first open channel for accommodating said doubled over lengthwise portion of said longer binaural tube means comprises a relatively thin spool-like member adapted for accommodating and holding said lengthwise portion of binaural tubing wrapped therearound; and,
an opening within said first open channel adjacent said spool-like member for insertion of said lengthwise portion of said longer binaural tube means prior to wrapping around said spool-like member.

4. A stethoscope as claimed in claim 3 wherein:
said spool-like member is comprised of two discs separated by a recessed thin cylindrical member and wherein said longer binaural tube means is seated against said cylindrical member.

5. A stethoscope as claimed in claim 4 further comprising:
retainment means within said first and said second open channels adapted for holding and retaining said binaural tube means.

6. A stethoscope as claimed in claim 5 wherein:
said binaural tube means is comprised of extruded plastic.

7. A stethoscope as claimed in claim 6 wherein said yoke, said ear tips and said stethoscope head are made of a molded plastic.

8. A stethoscope as claimed in claim 3 wherein said stethoscope head, said ear tips, said binaural tube means, and said yoke are formed of plastic materials.

9. A stethoscope as claimed in claim 3 wherein said binaural tube means have a length ratio in a range of about 0.63 to about 0.73.

10. A stethoscope as claimed in claim 7 wherein said yoke is provided with a plurality of slots crosswise of at least one channel for providing spring action to said yoke.

11. A stethoscope as claimed in claim 7 wherein said stethoscope head comprises a central channel in communication with a diaphram and in communication with two separate air passages adapted for connection with said separate binaural tube means.

12. A stethoscope comprising:
a stethoscope head;
a pair of ear tips;
binaural tube means extending from said head to said ear tips providing individually separate air passages of differing length from said stethoscope head to said ear tips;
a binaural yoke having a substantially U-shape and having channel members for receipt of said binaural tube means;
said binaural tube means extending from said stethoscope head being at least partly joined between said stethoscope head and said yoke;
said binaural tube means comprising two tubes including a longer tube and a shorter tube;
said yoke including first and second channel members; and,
at least a portion of each said channel members being sized to accommodate two widths of said tubes;
one of said first and second channel members of said yoke further comprises means for retaining a lengthwise portion of said longer tube for turning said lengthwise portion of said longer tube back on itself.

13. A stethoscope as claimed in claim 12 wherein said stethoscope head, said pair of ear tips, said binaural tube means, and said yoke are comprised of a plastic and wherein said binaural.

14. A stethoscope made of a plastic material comprising:
   a stethoscope head having two separate sound transmission tubes extending therefrom;
   a pair of ear tips;
   two binaural tubes including a longer tube and a shorter tube, each binaural tube extending from one of said sound transmission tubes of said stethoscope head to provide individually separate sealed air passages from said stethoscope head to said ear tips;
   a preformed binaural yoke having a substantially U-shape and having two channels adapted for receipt of said binaural tube means whereby said longer tube can be retained within said yoke without producing any sharp bends which would cause a loss of sound transmission;
   said yoke including first and second open channels extending from ear tip to ear tip;
   a spool-like member within one of said first and second open channels for being encircled by said longer binaural tube; and wherein;
   at least a portion of each said channel members is sized to accommodate two widths of said binaural tubes.

* * * * *